United States Patent
Gath et al.

(10) Patent No.: US 6,352,739 B1
(45) Date of Patent: Mar. 5, 2002

(54) CONTINUOUS MONITORING OF THE COATING OF A FILAMENTARY DIELECTRIC MATERIAL WITH ASSISTANTS

(75) Inventors: Rudolph Hans Gath, Mannheim; Klaus-Dieter Grammatik, Kaiserslautern; Hans-Joachim Weis, Mannheim; Dieter Lummel, Dirmstein, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/385,460

(22) Filed: Aug. 30, 1999

(30) Foreign Application Priority Data

Sep. 1, 1998 (DE) .......................... 198 39 816

(51) Int. Cl.$^7$ .................. G01B 7/06; G01B 121/02; B05D 1/40; B05D 3/14; B05D 7/24
(52) U.S. Cl. .................. 427/10; 427/9; 427/175; 73/160
(58) Field of Search .................. 427/8, 9, 10, 163.2, 427/175, 434.6, 434.7; 73/159, 160

(56) References Cited

U.S. PATENT DOCUMENTS

| | | | | |
|---|---|---|---|---|
| 3,777,127 A | * | 12/1973 | Goetchius et al. .......... 73/159 |
| 3,938,955 A | * | 2/1976 | Maggiolo .................... 73/159 |
| 4,042,724 A | * | 8/1977 | Nawracaj | |
| 4,066,558 A | * | 1/1978 | Shay et al. ................ 427/175 |
| 4,300,094 A | * | 11/1981 | Piso et al. | |
| 4,329,750 A | * | 5/1982 | Binnersley ............... 427/434.6 |
| 4,758,968 A | * | 7/1988 | Lord ......................... 73/160 |
| 4,900,496 A | * | 2/1990 | Andrews, Jr. et al. ... 427/434.6 |
| 5,352,483 A | * | 10/1994 | Humbrecht et al. ........ 427/175 |
| 5,386,195 A | * | 1/1995 | Hayes et al. .................. 427/10 |
| 5,801,538 A | * | 9/1998 | Kwon | |
| 5,912,078 A | * | 6/1999 | Schuette et al. ............ 427/175 |
| 6,120,833 A | * | 9/2000 | Bonnebat et al. | |

FOREIGN PATENT DOCUMENTS

DE 36 17 795 12/1987

* cited by examiner

Primary Examiner—Marianne Padgett
(74) Attorney, Agent, or Firm—Keil & Weinkauf

(57) ABSTRACT

A method for the continuous monitoring of the coating of a yarnlike dielectric material with assistants comprises applying a solution of said assistants dissolved in a polar solvent to said yarnlike material, then passing said yarnlike material between the electrodes of a downline capacitive measuring element, determining the capacity changes of said downline capacitive measuring element, and using said capacity changes to calculate the unevenness of the layer thickness of the applied solution.

10 Claims, 3 Drawing Sheets

CONTINUOUS MONITORING OF THE COATING OF A FILAMENTARY DIELECTRIC MATERIAL WITH ASSISTANTS

FIELD OF THE INVENTION

This invention relates to a method for the continuous monitoring of the coating of a filamentary dielectric material, especially a manufactured fiber, with assistants, such as spin-finish oils.

BACKGROUND AND PRIOR ART

The manufacture and further processing of fibers frequently necessitates coating the fibers with assistants. Typical cases are coating with spin-finish oils, for example winding oils, immediately following the spinning of the fibers or the application of flame retardants.

The evenness or unevenness of the application of the assistants to the fibers is of decisive importance for the further processing and quality of the fibers. To optimize the coating processes and also to quality-control the ongoing production, it would therefore be desirable to have a method for the continuous monitoring of coating of the fiber material. For the purposes of the present invention, unevenness is to be understood as meaning not only a qualitative statement about the constancy of the coating along the fiber but also a quantitative statement within the meaning of the statistical definition of the unevenness U $$U = \frac{1}{\bar{x} \cdot T} \int_0^T |x_i - \bar{x}| dt$$

where $\bar{x}$ is the mean, $x_i$ is the momentary value and T is the evaluation time for a given variable, for example the capacitance.

Instead of in terms of the unevenness U, irregularity is frequently also reported in terms of the coefficient of variation CV, which is defined as $$CV = \frac{1}{\bar{x}} \sqrt{\frac{1}{T} \int_0^T (x_i - \bar{x})^2 dt}$$

The coefficient of variation takes greater account of larger deviations from the mean than of smaller deviations, owing to the squaring within the integral. Insofar the text which follows refers generally to unevenness measurements, this is to be understood as encompassing a determination of the coefficient of variation or of some other comparable statistical variable.

From U.S. Pat. No. 4,845,983 and U.S. Pat. No. 4,862,741 an apparatus is known for measuring the unevenness of textile fibers by utilizing capacitive electrical methods of measurement to provide statistical information about the quality of fiber production. The device described in the above mentioned patents is commercialized under the trade name USTER®-TESTER by Swiss company Zellweger Uster AG. It determines the unevenness of a filamentary dielectric material by passing the filament between the electrodes of a capacitive measuring element, originally, the space between the electrodes contains only air or some other gas whose dielectric constant E is virtually 1. The introduction of the filamentary dielectric material increases the capacitance of the capacitor. If, then, as the filament passes through, variations in filament thickness occur, these give rise to corresponding variations in the capacitance of the measuring capacitor. The time profile of the capacitor's capacitance can finally be used to calculate the unevenness U or the coefficient of variation CV of the spun filament according to the abovementioned formulae.

However, this measuring principle is not suitable for determining the unevenness of fiber coatings, since, first, the thickness of the coating material is very small compared with the thickness of the fiber, so that unevennesses in the coating do not generate an analyzable signal in a capacitive measurement, especially not in a continuous on-line measurement of ongoing production. Secondly, in the case of manufactured fiber, the dielectric constants of the fiber material and the coating material are of the same order of magnitude. The substances in question are usually apolar, weakly polar or at best medium-polar substances. Accordingly, any capacitance changes detected in the measuring element are essentially dominated by the unevenness of the fibers themselves, so that it is impossible to say anything about possible unevennesses of the coating.

SUMMARY OF THE INVENTION

It is an object of the present invention to provide a method for the continuous monitoring of the coating of a filamentary dielectric material with assistants which through a simple nondestructive measurement enables an accurate determination to be made of the unevenness of the coating. The measurement shall be virtually inertialess so as to make possible even the continuous on-line monitoring of filaments produced on modern high-speed spinning machinery at a linear filament speed of 5000 m/min and more. The method of measurement shall be relatively simple, reliable and economical.

We have found that this object is achieved by a novel method for the continuous monitoring of the coating of a filamentary dielectric material with assistants, which comprises applying a solution of said assistants dissolved in a polar solvent to said filamentary material, then passing said filamentary material between the electrodes of a downline capacitive measuring element, determining the capacitance changes of said downline capacitive measuring element, and using said capacitance changes to calculate the unevenness of the layer thickness of the applied solution.

DETAILED DESCRIPTION

The underlying concept of this invention is accordingly that an even application of the solution is associated with an even coating of the filamentary material with assistants. It is therefore proposed according to the invention that the unevenness of the solution layer be determined immediately after the solution has been applied, without any wait until after the solvent has evaporated or been absorbed by the fiber before measuring the unevenness of the layer of assistant or assistants then present on the fiber. The invention exploits the fact that numerous assistants, although themselves apolar or only weakly polar, are soluble in polar solvents. For instance, the spin-finish oils LIMANOL ST24RN (Schill+Seilacher, Böblingen, Germany) or FASAVIN HA (Zschimmer & Schwarz, Lahnstein, Germany) are easy to prepare and apply to polyamide fibers as 10:90 oil/water mixtures. The solution applied to the fiber accordingly has a significantly higher dielectric constant than the fiber material itself. In the proposed measurement of capacitance changes due to the passing filament, the main signal is accordingly due to the applied solution and no longer due to the unevennesses of the fiber.

The method of the invention may utilize a very wide range of combinations of fiber material, solvent and assistant, provided the solvent has a higher dielectric constant than the fiber material.

In one advantageous embodiment of the method of the invention, said determining of said capacitance changes is effected by subtracting from the capacitance measured in said downline capacitive measuring element a reference capacitance previously determined for the uncoated filamentary material.

When the differences in dielectric constant are very large between the fiber material and the solvent, it is sufficient to use a reference capacitance which is a predetermined, constant value dependent only on the filament material and the average filament thickness. However, this method is unable to compensate for capacitance changes due to diameter variations of the moving filament, since the reference capacitance is always a constant value. But these variations are negligible in the case of widely different dielectric constants, since in this case capacitance changes are substantially due to unevennessses in the polar solvent layer.

For a more accurate measurement, the reference capacitance is continuously determined by passing said filamentary material between the electrodes of an upline capacitive measuring element prior to said applying of said solution, determining the capacitance changes of said upline capacitive measuring instrument and subtracting said capacitance changes from the capacitance changes measured using said downline capacitive measuring element by correlating the measured values in such a way that measured values associated with the same filament section are subtracted from each other in each case. This is preferably accomplished through electronic buffer storage of the values measured using the upline capacitive measuring element and subsequent electronic subtraction. This is because, as a filament section passes initially the upline capacitive measuring element and the respective capacitance change is measured at a certain time $t_1'$, it is possible to determine from the known filament speed v and the distance s between the upline and downline capacitive measuring elements the time difference $\Delta t$ after which this filament section will have reached the downline capacitive measuring element ($\Delta t=s/v$). Consequently, the capacitance change measured at the upline capacitive measuring element at time $t_1$ is substracted from the capacitance change measured at the downline capacitive measuring element at the time $t_1''=t_1'+\Delta t$. This method of measurement makes it possible for the individual diameter variations of the filament to be compensated. The method of measurement is therefore especially useful for such monitoring tasks where the dielectric constant difference between the solvent and the fiber material is relatively small.

For a particularly simple method of measurement constant voltage is applied to the capacitor and capacitance changes are detected by measuring charging and discharging currents. This is because the charge on a capacitor maintained at constant voltage is given by the relationship Q=CU, where Q is the charge, C is the capacitance and U is the voltage. If, then, the capacitance of the capacitor changes on account of the dielectric present between the electrodes of the capacitor changing with time, this will be associated with a change in the charge. This change in the charge can then be detected as the flow of a current.

Particularly sensitive and fast methods of measurement are made possible through RF impedance measurements where each capacitive measuring element combined with a normal inductor forms an electrical tuned circuit which is coupled to a conventional grid dip oscillator or, if instead of a valve a transistor is used for excitation, to a conventional transistor dipper.

The method of the invention is preferably used for monitoring the coating of manufactured fibers, for example of polyamides, such as nylon-6 or nylon-6,6. The polar solvent used is preferably water, since water has the very high dielectric constant of 80. However, it is also possible to use other polar solvents, for example alcohols or aqueous alcoholic solvents.

Useful assistants include a very wide range of compositions. The method is particularly preferably used for monitoring the coating of textile fibers with spin-finish oils, for example with winding oils. Typically, the winding oil will have been dissolved in water in a concentration of from 5 to 10%. The freshly spun polyamide filaments are initially moisture-free following their solidification in the quench chimney. Before being wound up, they have a water/winding oil system applied to them by means of a spin-finish application roll. The water evaporates later or is absorbed by the fiber. The spin-finish oil finally remains behind on the fiber.

We have determined that the method of the invention is particularly simple to carry out using conventional, commercially available unevenness measurement instruments such as the USTER®-TESTER already mentioned above.

The present invention accordingly also provides for the use of an apparatus for the capacitive unevenness measurement of fibers, especially an apparatus of the USTER® TESTER type, in a method for monitoring the coating of a filamentary dielectric material with assistants.

BRIEF DESCRIPTION OF THE DRAWINGS

An illustrative embodiment of the present invention will now be more particularly described by way of example with reference to the accompanying drawings, where.

DETAILED DESCRIPTION OF THE INVENTION WITH REFERENCE TO THE DRAWINGS

Figure 1:
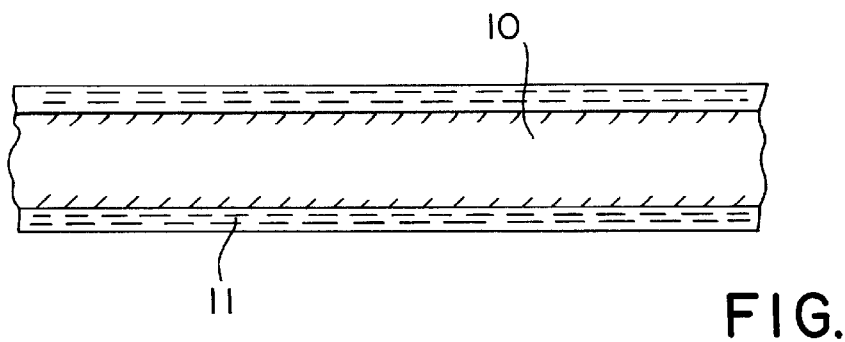
FIG. 1 shows a polyamide fiber in longitudinal section immediately following application of the spin-finish oil.
Figure 2:
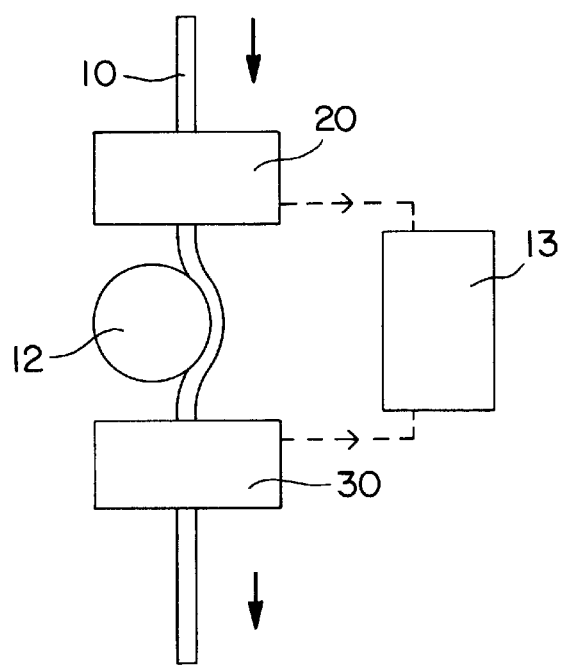
FIG. 2 shows a schematic representation of a measuring arrangement for carrying out the method of the invention.

FIG. 1 shows a partial longitudinal section through a freshly spun polyamide filament 10. After solidification in the quench chimney, said filament 10 is virtually moisture-free. Before being wound up, the filament has applied to it, by means of a spin finish application roll 12, a water/spin-finish oil mixture which forms a liquid film 11 on the fiber surface (FIG. 2). The water evaporates later or is at least partially absorbed by the fiber. The spin-finish oil remains as a thin coating on the fiber.

In a first embodiment of the method of the invention, a capacitive measuring cell 30 immediately downline of a spin finish application roll 12 detects the unevenness of the spin-finish oil coating. The measurement thus takes place at a time at which the water is still to evaporate and a relatively thick polar liquid film is present on the fiber surface.

Figure 3:
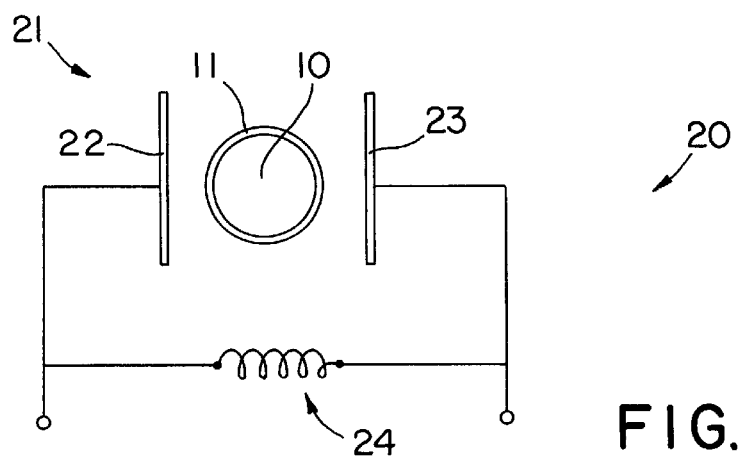
FIG. 3 shows a schematic representation of a capacitive measuring cell of the arrangement of FIG. 2.

According to the invention, the unevenness measurement is to be carried out using a capacitive measuring cell as diagrammatically depicted in FIG. 3 for the measuring cell 20; the measuring cell may have a corresponding construction. The measuring cell 20 is formed essentially by an open capacitor 21 through which the spin-finished filament 10 passes. The capacitance of the capacitor depends on the dielectric constant of the medium between the capacitor surfaces 22, 23 and is the total of the following contributions added together: the dielectric constant of the air ($\epsilon_0$), the dielectric constant of the polyamide fiber ($\epsilon_F$) and the dielectric constant of the applied layer ($\epsilon_S$). Changes in the thickness of the polyamide fiber 10 or in the thickness of the liquid layer 11 show up as a change in the total dielectric constant and hence also as a change in the capacitance of the capacitor 20.

When, for example, a constant voltage is applied to the capacitor 20, then changes in the capacitance will become evident as charging and discharging currents, which can be detected through a measurement of the current level.

Figure 4:
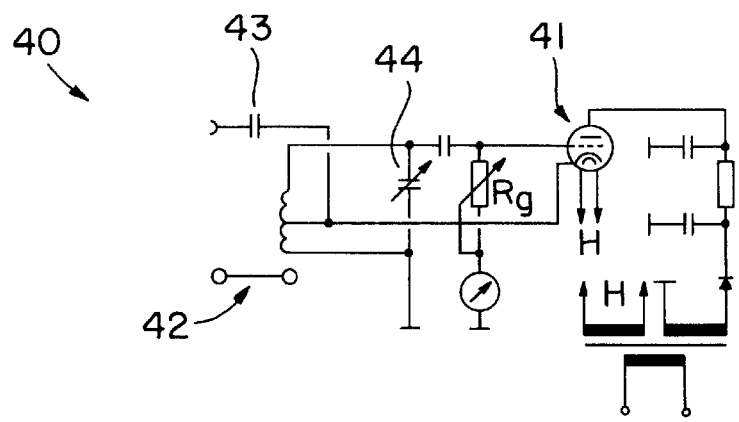
FIG. 4 shows a typical circuit of a grid dip oscillator.
Figure 5:
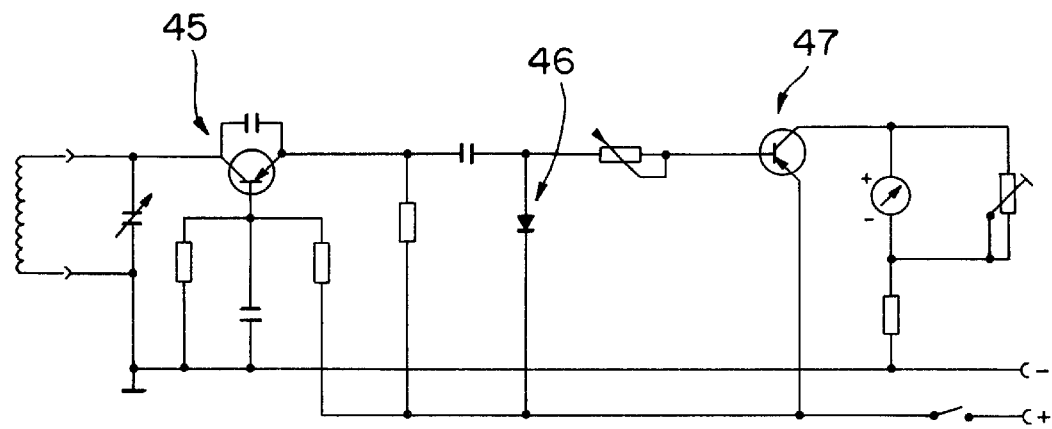
FIG. 5 shows the circuit of a two-stage transistor dipper.

However, an RF impedance measurement is preferable for accurate and inertia-free measurements on a high-speed filament 10 whose speed may be 5,000 m/min or higher. For this purpose, the capacitor 20 combines with the passing filament to form the capacitive part of a tuned circuit. As indicated in FIG. 3, the capacitor 20 may be connected up to a normal inductor 24, for example. This tuned circuit may for example be coupled to a grid dip oscillator 40, whose typical circuitry is depicted in FIG. 4. The tuned circuit of FIG. 3 represents the absorption circuit, while a calibrated-frequency profile tuned circuit excited by a valve 41 supplies the requisite energy. When both circuits are at resonance, the measuring circuit will lose energy and the grid current of the valve 41 will dip. The measuring circuit and the test circuit are coupled either directly or via a link line 42. However, capacitive coupling via the capacitor 43 depicted in FIG. 4 is also possible. The two circuits can be tuned to the same frequency via a variable capacitor 44 in the oscillator. The capacitance changes due to the passing filament will then become apparent as a change in the grid current. A similar circuit may also be constructed with transistors, as is schematically depicted in FIG. 5. This ensures in particular less dependence on the power supply. The primary variable measured is here initially the collector current at the transistor 45. However, the dip is too small for it to be reliably detectable. It is therefore advantageous to utilize the RF voltage applied to the tuned circuit and supply it via a small capacitor to a crystal diode 46. The corresponding DC voltage is used to drive a second transistor 47. In this case the quantity which is measured is the control voltage at the base of the downstream transistor, this control voltage being at a minimum at resonance and increasing in the event of the two tuned circuits being mistuned due to a change in the dielectric constant of the measuring cell.

In a preferred version of the method of the invention, the unevenness of the fiber is capacitively determined both before and after the application of the spin-finish oil. To this end, as depicted in FIG. 2, two measuring cells 20, 30 are provided. The values measured by the two measuring cells are digitized and evaluated by a microprocessor 13, The microprocessor 13 calculates a time-shifted difference signal from the values measured by the two measuring cells. The magnitude of the time shift depends on the path length As of the filament between the two measuring cells and the speed of the filament. The shift is chosen in such a way that the value measured by the upline measuring cell 20 has subtracted from it a value measured in the downline measuring cell 30 which was measured on the same section of fiber.

Figures 6A, 6B, 6C:
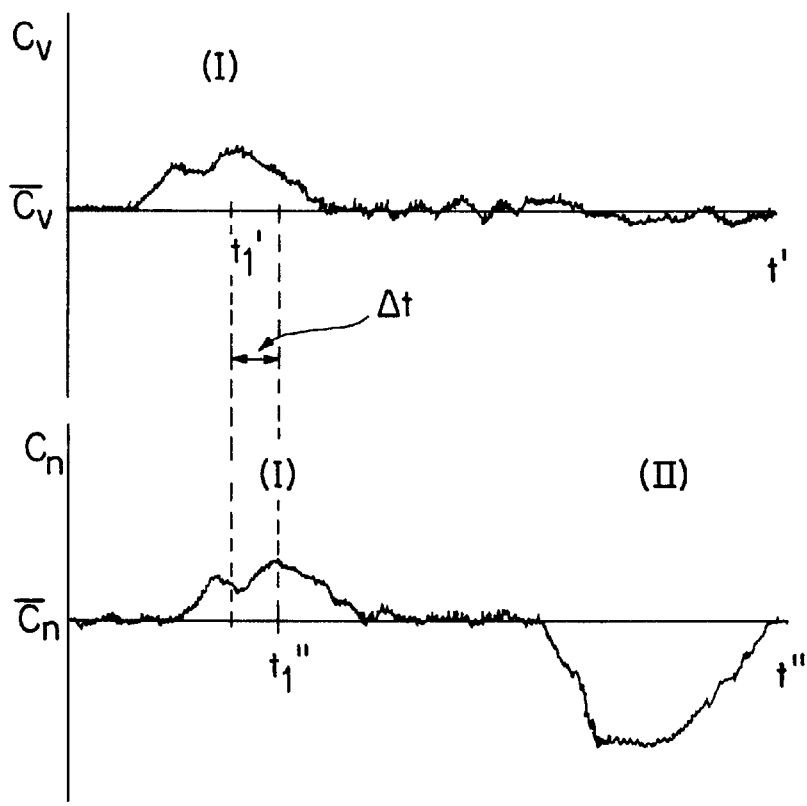
FIG. 6 shows a typical signal for measuring the capacitance change with time, FIG. 6a) schematically depicting the values measured by the upline measuring cell, FIG. 6b) schematically depicting the values measured by the downline measuring cell and FIG. 6c) schematically depicting the signal representing the difference between the measured values of FIG. 6a) and the measured values, shifted by $\Delta t$, from FIG. 6b).

FIG. 6 depicts the time profile of the capacitances in the measuring cells 20, 30. Given a known filament speed, the time axis may also be depicted as length axis, so that, ultimately, the "capacitance level" of a filament section is shown. As part of FIG. 6, FIG. 6a shows the measurements $C_v$ by the measuring cell 20 disposed upstream of the spin-finish oil applicator, while FIG. 6b shows the capacitance values $C_n$ of the measuring cell 30 disposed downstream of the spin-finish oil applicator. FIG. 6c shows the difference signal from the two measurements.

It can be seen in FIG. 6a that the time profile of the capacitance $C_v$ varies about a mean $\overline{C_v}$. The capacitance increases greatly in a region (I), indicating a local thickening of the fiber.

FIG. 6b tracing of the downline measuring cell is likewise observed to show an increase in the capacitance $C_n$ within the region (I). In addition, a distinct decrease in the capacitance is observed in the region (II). It is clear from FIG. 6b that a single post-coating measurement of the capacitance does not permit reliable inferences as to the cause of a measured unevenness.

It is only the difference signal $\Delta C$ from the two measurements, which is depicted in FIG. 6c, which makes it clear that it is only the decrease in the capacitance depicted in region (II) which is due to insufficient coating, while the capacitance change of region (I) is evidently due to an irregularity in the fiber itself.

The capacitance time profile depicted in FIG. 6 may also be statistically evaluated by the microprocessor 13 and, as indicated at the beginning, be characterized in terms of an unevenness U or a coefficient of variation CV for a certain period of measurement (i.e., for a certain length of filament).

The method of the invention can also be realized through the use of commercially available equipment for unevenness measurement, for example by means of an unevenness meter from USTER. Then, in the layout depicted in FIG. 2, the measuring cells 20 and 30 are each formed by an USTER instrument. If, as in FIG. 2, the measurement is carried out with an upline instrument and a downline instrument, the measurements can be read (via an interface usually present in commercial equipment) to a PC to form the difference between the two measurements and perform possible further statistical analysis.

We claim:

1. A method for continuously monitoring a process of coating a filamentary dielectric material with a solvent solution of a spin-finishing oil, in which said filamentary material and said solvent solution of a spin-finishing oil have dielectric constants of the same order of magnitude, which comprises applying said solvent solution of a spin-finishing oil dissolved in a polar solvent to said filamentary material, then immediately passing said filamentary material between electrodes of a downline capacitive measuring element which includes a capacitor, determining capacitance changes of said downline capacitive measuring element, and using said capacitance changes to calculate unevenness of layer thickness of said solution which has been applied.

2. A method as claimed in claim 1, wherein said determining of said capacitance changes is effected by subtracting from the capacitance measured in said downline capacitive measuring element a reference capacitance previously determined for said filamentary material prior to coating.

3. A method as claimed in claim 2, wherein said reference capacitance is a predetermined, constant value dependent on said filamentary material and the average thickness of said filamentary material.

4. A method as claimed in claim 2, wherein said reference capacitance is continuously determined by passing said filamentary material between the electrodes of an upline capacitive measuring element prior to said applying of said solution, determining the capacitance changes measured by said upline capacitive measuring instrument and subtracting said capacitance changes from the capacitance changes measured using said downline capacitive measuring element by correlating the measured values in such a way that measured values associated with the same filament section are subtracted from each other in each case.

5. A method as claimed in claim 1, wherein a constant voltage is applied to said capacitor and said capacitance changes are detected by measuring charging and discharging currents.

6. A method as claimed in claim 2, wherein each said capacitance measuring element forms part of an electrical tuned circuit.

7. A method as claimed in claim 1, wherein said filamentary material is a manufactured fiber.

8. A method as claimed in claim 1, wherein said polar solvent is water.

9. A method as claimed in claim 1, wherein an apparatus for capacitive unevenness measurement of fibers is used for monitoring said coating of said filamentary dielectric material with said spin-finishing oil.

10. A method as claimed in claim 4, wherein said both upline capacitive measuring element and said downline capacitive measuring element comprise an apparatus for capacitive unevenness measurement of fibers.

* * * * *